United States Patent [19]

Feldman et al.

[11] Patent Number: 5,126,455

[45] Date of Patent: Jun. 30, 1992

[54] PREPARATION OF SUBSTITUTED ALKALI METAL PIPERIDINE-4-CARBOXYLATES

[75] Inventors: Paul L. Feldman; Marcus F. Brackeen, both of Durham, N.C.

[73] Assignee: GLAXO Inc., Research Triangle Park, N.C.

[21] Appl. No.: 712,369

[22] Filed: Jun. 10, 1991

Related U.S. Application Data

[62] Division of Ser. No. 450,091, Dec. 31, 1989.

[51] Int. Cl.$^5$ .......................................... C07D 211/98
[52] U.S. Cl. ........................ 546/20; 546/215; 546/223
[58] Field of Search ................ 546/20, 215, 223

[56] References Cited

U.S. PATENT DOCUMENTS 3,518,275  6/1970  Griot et al. ........................ 546/20
3,993,470  11/1975  Devaux et al. .................... 546/223
3,998,834  6/1976  Janssen ............................. 546/223
4,179,569  2/1979  Janssen ............................. 546/223

OTHER PUBLICATIONS

*Chemical Abstract*, vol. 73 No. 19 #98869v, Winter et al "Synthesis of spirohydantoins from basic heterocyclic ketones" 1970.

*Primary Examiner*—C. Warren Ivy
*Assistant Examiner*—Raymond Covington
*Attorney, Agent, or Firm*—Salvatore R. Conte

[57] ABSTRACT

A method of preparing certain substituted alkali metal 4-carboxy-piperidine salts (I) by alkaline hydrolysis of certain novel substituted 1,3,8-triazaspiro[4.5]decane-2,4-diones (IV) which in turn are obtained from certain novel substituted chlorosulphonylamido piperidines (III).

10 Claims, No Drawings

PREPARATION OF SUBSTITUTED ALKALI METAL PIPERIDINE-4-CARBOXYLATES

The present invention relates to the preparation of substituted alkali metal 4-carboxy-piperidine salts, also known as substituted alkali metal piperidine-4-carboxylates, of the following formula:

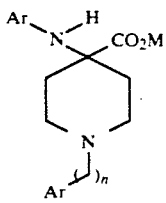
(I)

wherein Ar is phenyl (preferred), halophenyl, loweralkylphenyl, loweralkoxyphenyl or trifluoromethylphenyl, M is an alkali metal and n is the integer 1 or 2. Ar, in each instance, may be the same or different indicated function.

In the foregoing terms, "lower" is meant to indicate from 1 to about 4 straight or branched carbon atoms; and "halo" is generic to halogens of atomic weight less than 127, i.e., fluoro, chloro, bromo and iodo. Particular substituted phenyls are mono-substituted phenyls wherein the substituent is in the 2-position. Particular alkali metals are sodium, potassium and lithium.

The compounds of formula (I) are known useful intermediates in the preparation of the 4-anilidopiperidine class of opioid analgetics. For example, see the compound identified as number (XV) in the reaction scheme shown in column 15 of U.S. Pat. No. 3,998,834; and lines 5-10 in column 14, lines 64-65 in column 17, and lines 18-20 in column 47, of said patent. An additional disclosure of formula (I) compounds is found in Van Daele et al, Arzneim.-Forsch. (Drug Research) 26, No. 8, p. 1521-31 (1976). As shown in said references, the compounds of formula (I) are also useful in making other synthetic intermediates, such as, for example, the formula (VII-b-1) esters indicated at lines 30-35 in column 14 and the reaction scheme in column 15 of said patent.

The subject invention, which provides a novel alternate route for synthesizing the compounds of formula (I), comprises reacting an N-benzyl- or N-phenethyl-4-anilino-4-cyanopiperidine of formula (II) with chlorosulphonyl isocyanate in an inert organic solvent to yield the substituted chlorosulphonylamido piperidine of formula (III), as supported by NMR analysis The reaction is advantageously conducted at ambient temperatures (about 25° C.) although temperatures from about −10° C. to about 30° C. may be utilized to obtain quantitative yields. Suitable solvents include a halogenated hydrocarbon such as methylene chloride (preferred) or chloroform, an aromatic hydrocarbon such as benzene, toluene or xylene, an ether such as tetrahydrofuran or dioxane, and the like. The time required for the reaction will generally range from about 10 to about 60 minutes.

The thus-obtained (III) is treated with aqueous acid solution at elevated temperatures to effect solution of (III) and completion of the reaction, generally under reflux conditions. The acid may be either a strong mineral acid such as a hydrohalic acid (hydrochloric acid preferred), or sulfuric acid, or an organic acid such as acetic acid, p-toluenesulfonic or trifluoroacetic acid. Generally, the reaction is completed in 30 minutes to 2 hours. The reaction mixture, containing the substituted hydantoins of formula (IV) in the corresponding acid addition form, is then cooled to about 0°-5° C. and the pH is adjusted by addition of base, for example, sodium hydroxide, generally to about pH 5-5.5, to cause precipitation of the substituted hydantoins, or substituted 1,3,8-triazaspiro-[4.5]decane-2,4-diones, of formula (IV).

Alkaline hydrolysis of (IV) with appropriate base having an alkali metal cationic moiety (i.e., M) converts (IV) into the desired metal salt of formula (I). Typical bases include sodium hydroxide (preferred), potassium hydroxide, lithium hydroxide and the like. The hydrolysis is advantageously effected by heating (IV) in a sealed vessel with the base at elevated temperatures, generally from about 200° to about 250° C., for a time sufficient to complete the hydrolysis, generally for several hours. Upon cooling, precipitation of (I) occurs. Recovery and purification is accomplished according to conventional procedures.

The foregoing reaction sequences are illustrated by the following schematic diagram:

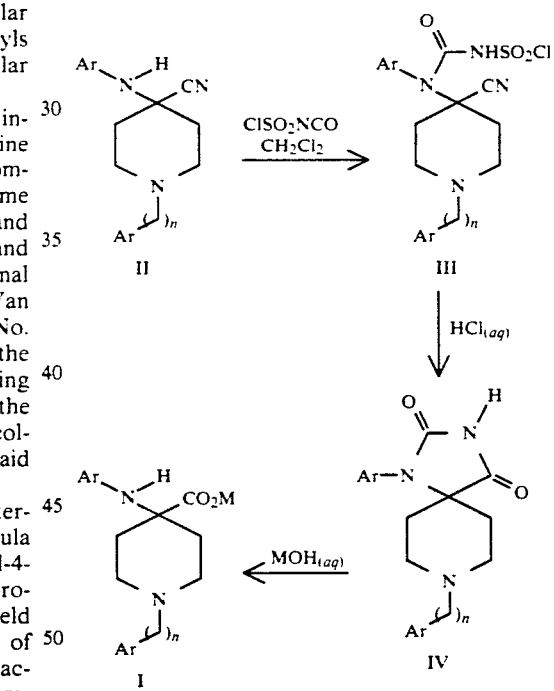

It is believed that the compounds of formula (III) and formula (IV) are not only useful intermediates in the foregoing reaction scheme but are also novel compounds. As such, they constitute an additional aspect of the subject invention. In addition, the respective syntheses of (III) and (IV), as described herein, also constitute further aspects of the subject invention. Further novel compounds are the hydantoins of formula (IV) in acid addition salt form. Such salts, which are readily obtainable by conventional treatment of (IV) with mineral or organic acids, may be utilized as intermediates in the synthesis of (I), for example, by treatment with sufficient base to affect the alkaline hydrolysis previously described.

EXAMPLE 1

N-benzyl-4-cyano-4-(N-chlorosulfonylamido)-phenylamino]piperidine

To a solution of N-benzyl-4-anilino-4-cyanopiperidine (93 2 g, 0.32 mol) in methylene chloride (1L, dried by distilling from $CaH_2$) is added chlorosulphonyl isocyanate (27.8 ml, 0.32 mol) dropwise maintaining the temperature between 20°-30° C. with a water bath. A precipitate forms immediately. Following the addition of all of the chlorosuphonylisocyanate, the reaction is stirred an additional 30 minutes. Concentration of the mixture yields N-benzyl-4-cyano-4-[(N-chlorosulfonylamido)phenylamino] piperidine (NMR analysis) as a white solid; yield 138.5 g (100%).

EXAMPLE 2

8-Benzyl-1-phenyl-1,3,8-triazaspiro[4.5]decane-2,4-dione

To the solid obtained in Example 1 is added 1N HCl (1L) and the resulting mixture is heated at 90° C. at which point a solution is obtained. The solution is heated to reflux for 1 hour and then cooled to 0° C. To the chilled solution is added 5N NaOH with stirring until a pH of 5.5 is reached whereupon precipitation of a solid occurs. The solid is filtered, washed with ether, and dried in a vacuum oven to give 8-benzyl-1-phenyl-1,3,8,-triazaspiro[4.5]decane-2-4-dione; yield: 64.5 g, (60%); m.p. 290° C. (dec). An analytical sample is prepared by recrystallizing the solid from methanol; m.p. 259°-260° C. Anal Calcd for $C_{20}H_{21}N_3O_2$; C, 71.6; H, 6.3; N, 12.5%. Found: C, 71.7; H, 6.3; N, 12.6%.

EXAMPLE 3

Sodium 4-carboxy-4-phenylamino-N-benzylpiperidine

In a 340 ml capacity sealed bomb reactor equipped with a mechanical stirrer is added 8-benzyl-1-phenyl-1,3,8,-triazaspiro-[4.5]decane-2-4-dione (64.0 g 0.19 mol), sodium hydroxide (46.0 g, 1.15 mol), and water (150 ml). The vessel is heated at 225° C. with stirring for 18½ hours. The reaction is then cooled to 0° C. and the resultant solid filtered and dried in a vacuum oven to give sodium 4-carboxy-4-phenylamino-N-benzylpiperidine; mp>300° C.

EXAMPLE 4

By repeating the procedure of Example 1, except that an equivalent amount of an appropriately substituted cyanopiperidine is utilized as the starting material to be reacted with chlorosulphonyl isocyante, the following respective compounds of formula (III) are prepared
N-phenethyl-4-cyano-4-[(N-chlorosulfonylamido)-phenylamino]piperidine;
N-(2'-trifluoromethylbenzyl)-4-cyano-4-[(N-chlorosulfonylamido)phenylamino]-piperidine;
N-(2'-methylbenzyl)-4-cyano-4-[(N-chlorosulfonylamido)-2'-methylphenylamino]piperidine;
N-(2'-ethoxyphenethyl)-4-cyano-4-[(N-chlorosulfonamido)phenylamino]piperidine;
N-(2'-chlorobenzyl)-4-cyano-4-[(N-chlorosulfonamido)-2'-chlorophenylamino]piperidine;
N-phenethyl-4-cyano-4-[(N-chlorosulfonylamido)-2'-trifluoro-methylphenylamino]piperidine; and
N-benzyl-4-cyano-4-[(N-chlorosulfonylamido)-2'-methoxyphenylamino]piperidine.

EXAMPLE 5

The procedure of Example 2 is repeated except that an equivalent amount of each compound of formula (III) identified in Example 4 is substituted for the particular piperidine starting material utilized therein to yield the following respective substituted hydantoins of formula (IV):
8-phenethyl-1-phenyl-1,3,8-triazaspiro[4.5]decane-2,4-dione;
8-(2'-trifluoromethylbenzyl)-1-phenyl-1,3,8-triazaspiro[4.5]decane-2,4-dione;
8-(2'-methylbenzyl)-1-(2'-methylphenyl)-1,3,8-triazaspiro[4.5]decane-2,4-dione;
8-(2'chlorobenzyl)-1-(2'-chlorophenyl)-1,3,8-triazaspiro[4.5]decane-2,4-dione;
8-phenethyl-1-(2'trifluoromethylphenyl)-1,3,8-triazaspiro[4.5]decane-2,4-dione;
8---benzyl-1-(2'-methoxyphenyl)-1,3,8-triazaspiro[4.5]-decane-2,4-dione;

EXAMPLE 6

By following the procedure of Example 3, except that an equivalent amount of each compound of formula (IV) identified in Example 5 is subjected to alkaline hydrolysis with an equivalent amount of the appropriate alkali metal hydroxide, the following respective salts of formula (I) are prepared:
sodium 4-carboxy-4-phenylamino-N-phenethylpiperidine;
potassium 4-carboxy-4-phenylamino-N-(2'-trifluoromethylbenzyl)piperidine;
sodium 4-carboxy-4-(2'-methylphenyl)amino-N-(2'-methylbenzyl)piperidine;
sodium 4-carboxy-4-phenylamino-N-(2'-ethoxyphenethyl)-piperidine;
sodium 4-carboxy-4-(2'-chlorophenyl)amino-N-(2'-chlorobenzyl)piperidine
potassium 4-carboxy-4-(2'-trifluoromethylphenyl)amino-N-phenethyl-piperidine; and
lithium 4-carboxy-4-(2'-methoxyphenyl)amino-N-benzylpiperidine

What is claimed is:

1. A substituted 1,3,8-triazaspiro[4.5]decane-2,4-dione of the formula:

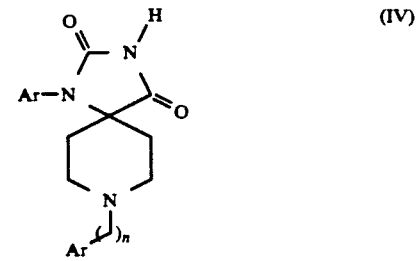

wherein each Ar is phenyl, halophenyl, loweralkylphenyl, lower-alkoxyphenyl or trifluoromethylphenyl and n is the integer 1 or 2, and the acid addition salts thereof.

2. 8-Benzyl-1-phenyl-1,3,8-triazaspiro[4,5-decane)-2,4-dione.

3. The method of preparing a substituted 1,3,8-triazaspiro[4,5]decane-2,4-dione of the formula:

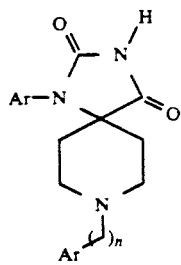

(IV)

wherein each Ar is phenyl, halophenyl, loweralkylphenyl, loweralkoxyphenyl or trifluoromethylphenyl, and n is the integer 1 or 2, which comprises treating a substituted chlorosulphonylamido piperidine of the formula:

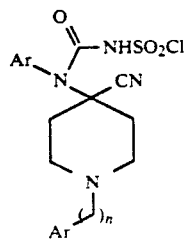

(III)

with aqueous acid solution at elevated temperature, followed by cooling and adjustment of the pH with base, to yield said substituted 1,3,8-triazaspiro[4,5]-decane-2,4-dione.

4. The method of claim 3 for preparing 8-benzyl-1-phenyl-1,3,8-triazaspiro[4,5]decane-2,4-dione which comprises treating N-benzyl-4-cyano-4-[(N-chlorosulfonylamido)phenylamino]piperidine with hydrochloric acid solution under reflux, followed by cooling to about 0°–5° C. and adjustment of the pH with sodium hydroxide to about pH 5–5.5, to yield said 8-benzyl-1-phenyl-1,3,8-triazaspiro-[4,5]decane-2,4-dione.

5. The method of claim 3 wherein said substituted chlorosulphonylamido piperidine of formula (III) is obtained by reacting a substituted 4-cyanopiperidine of the following formula (II):

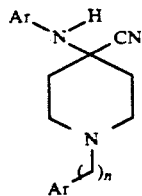

(II)

with chlorosulphonyl isocyanate in an inert organic solvent.

6. The method of preparing 8-benzyl-1-phenyl-1,3,8-triazaspiro[4.5]decane-2,4-dione which comprises:

(a) reacting N-benzyl-4-anilino-4-cyanopiperidine with chlorosulphonyl isocyanate in methylene chloride to yield N-benzyl-4-cyano-4-[(N-chlorosulfonylamido)phenylamino]piperidine;

(b) and treating said N-benzyl-4-cyano-4-[(N-chlorosulfonylamido)phenylamino]piperidine with hydrochloric acid solution under reflux, followed by cooling to about 0°–5° C. and adjustment of the pH with sodium hydroxide to about pH 5–5.5, to yield said 8-benzyl-1-phenyl-1,3,8-triazaspiro-[4,5]decane-2,4-dione.

7. A substituted chlorosulphonylamido piperidine of the following formula:

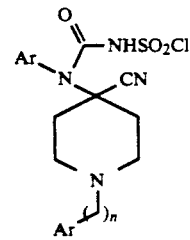

wherein each Ar is phenyl, halophenyl, loweralkylphenyl, loweralkoxyphenyl or trifluoromethylphenyl and n is the integer 1 or 2.

8. N-Benzyl-4-cyano-4-[(N-chlorosulfonylamido)-phenylamino]piperidine.

9. The method of preparing a substituted chlorosulphonylamido piperidine of the following formula:

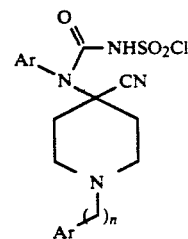

(III)

wherein each Ar is phenyl, halophenyl, loweralkylphenyl, loweralkoxyphenyl or trifluoromethylphenyl and n is the integer 1 or 2, which comprises reacting a substituted 4-cyano-piperidine of the following formula:

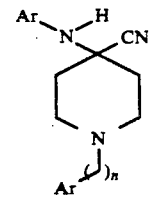

(II)

with chlorosulphonyl isocyanate in an inert organic solvent to yield said substituted chlorosulphonylamido piperidine.

10. The method of claim 9 for preparing N-benzyl-4-cyano-4-[(N-chloro-sulfonylamido) phenylamino]-piperidine which comprises reacting N-benzyl-4-anilino-4-cyanopiperidine with chlorosulphonyl isocyanate in an inert organic solvent to yield said N-benzyl-4-cyano-4-[(N-chlorosulfonylamido)phenylamino]piperidine.

* * * * *